United States Patent [19]

Patel et al.

[11] Patent Number: 4,863,970

[45] Date of Patent: Sep. 5, 1989

[54] PENETRATION ENHANCEMENT WITH BINARY SYSTEM OF OLEIC ACID, OLEINS, AND OLEYL ALCOHOL WITH LOWER ALCOHOLS

[75] Inventors: Dinesh C. Patel, Murray, Utah; Yunik Chang, Lakewood, N.J.

[73] Assignee: Theratech, Inc., Salt Lake City, Utah

[21] Appl. No.: 218,702

[22] Filed: Jul. 13, 1988

Related U.S. Application Data

[63] Continuation-in-part of Ser. No. 930,764, Nov. 14, 1986, abandoned.

[51] Int. Cl.$^4$ .................... A01N 61/00; A61K 31/00
[52] U.S. Cl. .................... 514/784; 514/947; 514/772; 514/785; 514/786
[58] Field of Search .................. 424/59; 514/946, 947, 514/69, 784, 785, 786, 772

[56] References Cited

U.S. PATENT DOCUMENTS

| | | | |
|---|---|---|---|
| 4,379,454 | 4/1983 | Campbell | 424/448 |
| 4,381,307 | 4/1983 | Sloan | 514/192 |
| 4,460,372 | 7/1984 | Campbell et al. | 424/449 |
| 4,537,776 | 8/1985 | Cooper | 514/424 |
| 4,552,872 | 11/1985 | Cooper et al. | 514/174 |
| 4,557,934 | 12/1985 | Cooper | 514/159 X |
| 4,588,580 | 5/1986 | Gale et al. | 424/449 |
| 4,593,048 | 6/1986 | Sato et al. | 514/778 |
| 4,764,379 | 8/1988 | Sanders | 424/449 |

FOREIGN PATENT DOCUMENTS

| | | |
|---|---|---|
| 0043738 | 1/1982 | European Pat. Off. . |
| 0095813 | 12/1983 | European Pat. Off. . |
| 0117080 | 3/1984 | European Pat. Off. . |
| 2153223 | 8/1985 | United Kingdom . |

OTHER PUBLICATIONS

Drug Delivery Systems, R. L. Juliano, "Characteristics and Biomedical Applications", 1980, p. 159.
Jane Stotts and W. Jeanne Ely, "Induction of Human Skin Sensitization to Ethanol", 1977, pp. 69:219-222.
William Brown et al., "Comparative Ultrastructure & Cytochemistry of Epidermal Responses to Tape Stripping, Ethanol & Vitamin A Acid in Hairless Mice", 1979, 73:203-206.

Primary Examiner—John F. Terapane
Assistant Examiner—Catherine S. K. Scalzo
Attorney, Agent, or Firm—Thorpe, North & Western

[57] ABSTRACT

Penetration-enhancing pharmaceutical compositions for topical transepidermal and percutaneous application are disclosed which are non-irritating to the skin. These compositions are made up of a safe and effective amount of an active pharmaceutical permeant, including hydrophilic salt forms, contained in a novel penetration-enhancing vehicle comprising, (i) 1-95% w. of a cell-envelope disordering compound selected from the group consisting of oleic acid, oleyl alcohol, glycerol monoleate, glycerol dioleate, glycerol trioleate and mixtures thereof, (ii) 5-75% w., and preferably 5-49% w., of a lower alkanol selected from the group consisting of ethanol, propanol and isopropanol and mixtures thereof and (iii) 0-45% w., and preferably 1-45% w., of an inert diluent which, according to properties of the permeant used, may range from hydrophilic to hydrophobic. Water, polyethylene or polypropylene glycols and mineral oil are exemplary diluents.

40 Claims, No Drawings

PENETRATION ENHANCEMENT WITH BINARY SYSTEM OF OLEIC ACID, OLEINS, AND OLEYL ALCOHOL WITH LOWER ALCOHOLS

BACKGROUND OF THE INVENTION

This invention is a continuation-in-part of Ser. No. 06/930,764, filed Nov. 14, 1986 now abandoned.

This invention relates to compositions which enhance the penetration of pharmaceutically-active agents through the integument. More particularly, this invention relates to binary combinations of certain penetration enhancers which facilitate percutaneous and transepidermal delivery of a broad range of pharmaceutically-active agents.

The resistance of the skin to being penetrated by pharmaceutically-active agents is well documented. As compared to mucosal tissues, the stratum corneum is compact and highly keratinized. The lipids and proteins of the stratum corneum, although relatively thin, is compact and quite impermeable. Such impermeability of the skin is highly essential to the well being of a living organism in that it serves as a barrier to the ingress of pathogens and toxic materials, and the egress of physiologic fluids.

The impermeability of pharmaceutical agents through the skin is due to the nature of the very thin stratum corneum layer which is only 10-15 cells, i.e. about 10 microns thick. This layer is formed naturally by cells migrating toward the skin surface from the basal layer. Cells slowly move from the basal layer to the surface where they are sloughed off. As they progress toward the surface they become progressively more dehydrated and keratinized.

Because of the advantages of dermal application of pharmaceutically-active agents, various penetration enhancers have been sought. A penetration enhancer is one or more compounds which alter the skin as a barrier to increase the flux of a desired pharmaceutical permeant across the skin.

Penetration enhancers have been primarily categorized according to their ability to enhance permeant flux via three pathways. The first is the continuous polar or aqueous pathway composed of proteins. It is thought that solvent swelling or protein conformational changes provide the key to altering the penetration of the polar pathway. Surfactants alter the transport of polar permeant molecules to a much greater extent than the transport of nonpolar permeants. Solvents such as DMSO, 2-pyrrolidone and dimethylformamide can swell the stratum corneum to also enhance the polar pathway.

The second pathway is a continuous non-polar pathway consisting of lipids. The key to altering this pathway appears to be fluidizing the lipids which, in the stratum corneum, appear to be crystalline. Solvents such as DMSO, 2-pyrrolidone, and dimethylformamide, previously mentioned also appear able to solubilize or fluidize lipids. Other solvents include diols such as glycerol and propylene glycol.

The third pathway is a heterogeneous polar-nonpolar multilaminate of lipids and proteins. Binary vehicles appear best suited to act as enhancers on this multilaminate pathway. Prior art binary systems consist of a particular category of a polar solvent combined with a variety of compounds generally referred to as "cell-envelope disordering compounds".

U.S. Pat. No. 4,537,776, Cooper, issued Aug. 27, 1985, contains an excellent summary of prior art and background information detailing the use of certain binary systems for permeant enhancement. Because of the completeness of that disclosure, the information and terminology utilized therein are incorporated herein by reference. That patent teaches using a binary system wherein N-(2-hydroxyethyl) pyrrolidone is used as the solvent and the cell-envelope disordering compounds are selected from the group consisting of methyl laurate, oleic acid, oleyl alcohol, moloolein, myristyl alcohol and mixtures thereof.

Similarly, European Patent Application No. 43,738, published Jan. 13, 1982, teaches using selected diols as solvents along with a broad category of cell-envelope disordering compounds for delivery of lipophilic pharmacologically-active compounds. This reference also teaches that cosmetically acceptable solvents may also be combined with permeant and the diol and cell-envelope disordering compounds provided the solvent evaporates rapidly and completely to leave only the active components of the composition at the site of application. The acceptable solvents are stated to be ethanol or isopropanol. Because of the detail in disclosing the cell-envelope disordering compounds and the diols, the disclosure of European Patent Application No. 43,738 is also incorporated herein by reference.

Most of the cell-envelope disordering compounds mentioned in these publications are unsaturated lipid components having polar head groups.

A binary system for enhancing metoclopramide penetration is disclosed in UK Patent Application No. GB 2,153,223 A, published Aug. 21, 1985 and consists of a monovalent alcohol ester of a C8-32 aliphatic monocarboxylic acid (unsaturated and/or branched if C18-32) or a C6-24 aliphatic monoalcohol (unsaturated and/or branched if C14-24) and an N-cyclic compound such as 2-pyrrolidone, N-methylpyrrolidone and the like. It is postulated that the N-cyclic compound serves a solvent function which carries the active agent whereas the esters or alcohols serve as adjuvants to open up the stratum corneum, i.e. as cell-envelope disordering compounds.

In referring to the epidermal permeability of lower alkanols, Drug Delivery Systems, Characteristics and Biomedical Applications, Oxford University Press, NY, 1981, edited by R. L. Juliano, teaches at page 159 that simple alcohols through n-butanol have epidermal permeabilities no different than that of water. However, U.S. Pat. Nos. 4,379,454 to Campbell et al,; Campbell et al, 4,460,372 and Gale et al, 4,588,580 refer to the use of gelled ethanol as an enhancer in specialized transdermal or percutaneous drug delivery devices.

U.S. Pat. No. 4,593,048, Sato, issued June 3, 1986, shows skin permeation of drugs using a system consisting of a major amount of a lower alcohol having 1 to 4 carbon atoms and a minor amount of an adjuvant consisting of (1) a saturated straight chained, branched chained or cyclic aliphatic hydrocarbon containing 5 to 20 carbon atoms which may be optionally halogen substituted, (2) a carboxylic acid ester containing 13 to 24 carbon atoms wherein the acid moiety contributes 12 to 18 carbon atoms and the alcohol moiety is from 1 to 6 and preferably from 3 to 6 carbon atoms and (3) an ether containing 8 to 16 carbon atoms. The adjuvant is incorporated in amounts ranging from 1 to 50 percent by weight, and preferably 5 to 30 percent by weight, based on the lower alcohol.

From the above cited art and incorporated disclosures, it is apparent that some binary enhancers favor lipophilic permeants. There appears to be no recognition of an enhancer system that favors the penetration of salts and other hydrophilic permeants. Moreover, those binary systems containing diols and N-cyclic solvents may cause considerable skin irritation even at low concentrations. However, diols or N-cyclic solvents are taught to be necessary components of a binary system. In general, simple alcohols are taught to be solvents or cosolvents to help bring various mixtures into solution but are to be evaporated rapidly from the skin surface and do not function as penetration enhancers any better than water.

A problem associated with use of high amounts of lower alcohols, i.e. above about 50%, is that they are known to induce human skin sensitization and have been stated to be unsuitable as solvents for compounds applied to the skin. See, for example, Stotts, et al, Induction of Human Skin Sensitization to Ethanol, J. of Investigative Dermatology, 69:219–222 (1977) and Brown et al, Comparative Ultrastructure and Cytochemistry of Epidermal Responses to Tape Stripping, Ethanol and Vitamin A Acid in Hairless Mice, J. of Investigative Dermatology 73:203–206 (1979).

Other patents or publications relating to transdermal administration of active permeants are Cooper, European Patent Application No. 95,813,A2, published July 12, 1983, entitled Penetrating Topical Pharmaceutical Compositions Containing 9-(2-Hydroxyethoxymethyl)-Guanine; Durrant et al, European Patent Application No. 117,080, published Aug. 29, 1984, entitled Skin Treatment Composition.

SUMMARY OF THE INVENTION

The present invention relates to improved compositions and methods for improving the penetration of a broad category of pharmaceutically-active agents which are lipophilic or hydrophilic including salts and which produce little or no skin irritation to human or animal tissue systems. The invention provides penetrating topical compositions based on the use of a pharmaceutically-active agent dissolved in, or admixed with, a penetration-enhancing binary mixture of (a) about 1 to 95% by weight of one or more cell-envelope disordering compounds selected from the group consisting of oleic acid, oleyl alcohol, glycerol monooleate, glycerol dioleate and glycerol trioleate and mixtures thereof and (b) 5–75%, and preferably 5–49%, by weight of a $C_2$ or $C_3$ lower alcohol. In addition, the formulation can optionally contain 0 to 45% by weight of inert ingredients which are soluble within the enhancer composition. Such ingredients can vary from hydrophilic to hydrophobic depending upon the desired combination. Representative inert ingredients include water, polypropylene glycol, polyethylene glycol, polyvinyl alcohols, polyvinylpyrrolidone, mineral oil, silicone oil, ethylene-vinyl acetate polymers or other low molecular weight polymers soluble in water, lower alcohols or suitable oils.

By employing this binary mixture with or without optional inert ingredients, it has been found that significant penetration of salts and other hydrophilic permeants as well as lipophilic permeants is obtained and that skin irritation often associated with cell-envelope disordering compounds and/or solvents is essentially nonexistent.

The invention is therefore not limited to any specific category or categories of permeants but is inclusive of all therapeutically active compounds and their use which are responsive by being incorporated into the binary mixture as more fully set forth herein.

Also, the invention is drawn to treatment methods by means of which an effective amount of a permeant, combined with the binary mixture, is topically applied to a human or animal subject.

DETAILED DESCRIPTION OF THE INVENTION

The following definitions, when used and as they apply to the present invention, are consistent with those contained in U.S. Pat. No. 4,537,776.

By "topical administration" or "topical application" is meant directly laying or spreading upon epidermal tissue, especially outer skin or membrane, including the skin or membrane of the oral or vaginal cavities.

By "safe and effective", is meant a sufficient amount of the permeant composition to provide the desired systemic effect and performance, or local activity, or both at a reasonable benefit/risk ratio attendant any medical treatment Within the scope of sound medical judgment, the amount of permeant used will vary with the particular condition being treated, the severity of the condition, the duration of the treatment, the specific permeant compound employed, its concentration, the condition of the patient, concurrent therapies being administered and other factors within the knowledge and expertise of the patient or the attending physician or other practitioner.

By "toxicologically- or pharmaceutically-acceptable" is meant the pharmaceutical actives (or permeants), as well as the other compatible drugs, medications or inert ingredients which the term describes, are suitable for use in contact with the tissues of humans and animals without undue toxicity, irritation, allergic response, and the like commensurate with a reasonable benefit/risk ratio.

By the terms "comprising" is meant that various other compatible drugs and medicaments, as well as inert ingredients, occlusive agents, and cosmetic vehicles, can be conjointly employed in the compositions and methods of this invention, as long as the critical binary penetration enhancement vehicle and pharmaceutically active permeant are used.

By "afflicted situs" is meant a localized area of pathology, discomfort, infection, inflammation or lesion, and the immediately surrounding area.

By "application situs" is meant a site suitable for topical application with or without he means of a mechanical sustained release device, patch or dressing, e.g. behind the ear, on the arm, back, chest, stomach, leg, top of foot, etc.

By "penetration-enhancing" is meant that the binary penetration enhancing carriers or vehicles of this invention with or without optional inert ingredients provide marked transepidermal or percutaneous delivery of an incorporated active permeant, when compared to other compositions at equal chemical potential. Equal chemical potential is important since varying solubilities of drugs in different carrier vehicles will affect their transport across skin. As stated in U.S. Pat. No. 4,537,776, if a drug is soluble in vehicle A to the extent of 24%, and in vehicle B to the extent of 4%, were the compositions to be compared at equal percentage concentration, rather than equal chemical potential, the lower solubility carrier would show a misleading six-fold difference in transport over the more soluble vehicle. Therefore, the simplest way of assuring equal chemical potential for evaluating penetration enhancement is to use saturated solutions or solutions of equal percentage of saturation of active permeants in the various enhancer combinations, e.g. 50% saturated. In the examples used herein, unless stated otherwise, the enhancer combinations are saturated with the active permeant components.

As used herein, all percentages and ratios are by weight of the total composition unless otherwise specified.

The terms "permeant", "active", "pharmaceutical active", "pharmacological active", "pharmaceutical agent", "pharmacological agent", "pharmaceutically-, or pharmacologically-active agent", "chemical agent", "therapeutic agent", and "drug", are used interchangeably herein.

The compositions of this invention require, at a minimum, a permeant capable of producing systemic effects, or producing or possessing local activity, in a binary vehicle or carrier comprising a cell-envelope disordering compound selected from the group consisting of oleic acid, oleyl alcohol, glycerol monoleate, glycerol dioleate, glycerol trioleate and mixtures thereof, and a lower alcohol selected from the group consisting of ethyl alcohol, propyl alcohol or isopropyl alcohol with or without optional inert ingredients within the stated concentration ranges.

The composition may also contain other optional components which enhance their cosmetic appeal or acceptability, i.e., thickeners, pigments, fragrances, perfumes, and the like. The binary penetration combinations are essentially free of skin irritation characteristics. However, a permeant combined with the penetration enhancers may cause some irritation. Therefore, if desired, other components which tend to reduce skin irritation may be incorporated into the compositions.

BINARY PENETRATION ENHANCEMENT VEHICLES

The binary penetration enhancement combinations of the present invention significantly enhance the penetration of a host of pharmaceutically-active permeants including salts. These permeants may be lipophilic or hydrophilic or partially lipophilic or hydrophilic.

The binary combinations comprise one or more of the stated cell-envelope disordering compounds and a lower alkanol selected from the group consisting of ethanol, propanol and isopropanol with or without the optional inert ingredients.

While certain cell envelope disordering compounds are known in the art previously cited, it has been found that oleic acid, oleyl alcohol and glycerol esters of oleic acid used separately or in combination provide for excellent skin penetration of active permeants when combined with lower alcohols within the stated concentration ranges. Preferred combinations are (a) oleic acid or oleyl alcohol in combination with lower alcohols; (b) glycerol esters of oleic acid mixed with oleic acid or oleyl alcohol in combination with lower alcohols; (c) glycerol esters of oleic acid in combination with lower alcohols; (d) mixtures of oleic acid and oleyl alcohol in combination with lower alcohols and (e) mixtures of oleic acid and oleyl alcohol mixed with glycerol esters of oleic acid.

Since all of the above are derivatives of oleic acid in that they are either oleic acid per se, esters of oleic acid or the alcohol resulting from the reduction of oleic acid, they will collectively be referred to as the "oleic group". It is realized that there are many other oleic acid derivatives, i.e. methyl oleate and other esters, oleamide and other amides, olealdehyde, etc. which could be classified as being of the oleic group. However, for purposes of description of the present invention the terms "oleic group" is believed to be sufficiently limited to oleic acid, glycerol esters of oleic acid and oleyl alcohol and all combinations thereof.

The members of the oleic group may be present in concentrations that vary widely in the penetration enhancer combination. They may range between about 1 to 95% by weight of the overall binary penetration enhancer combination.

The concentration of the lower alcohols has been found to be more limited and generally ranges between about 5 and 75% by weight of the penetration enhancer combination. At concentrations above about 50% by weight, as noted above, lower alcohols can cause skin irritation and one may also become sensitized to the alcohols. However, when used in the present combination with oleic group compounds, skin irritation is significantly reduced. In most cases, it is preferred to maintain the alcohol concentration in the enhancer combination between about 5 and 49% by weight and most preferably between about 20 and 49% by weight.

Although the enhancer combination is referred to as "binary", it is often preferable to add an optional third inert component when it is desired to maximize the effectiveness of the binary oleic group and lower alcohol components with any given active permeant and retain the lower alcohol within the desired range of 75%, and preferably 49%, and below. Thus, it is often desirable to incorporate an inert ingredient to make up from about 0 to 45% by weight of the overall penetration enhancer and preferably between about 1 and 45% by weight. Such third component can be any compatible inert ingredient which is soluble in the oleic group-lower alcohol enhancer combination. Such ingredient may be hydrophilic or hydrophobic depending upon the enhancer combination and the active permeant to be used. The invention is not limited to any particular inert ingredient as such will be readily ascertainable by one skilled in the art. Typical of such inert ingredients are water, polypropylene glycol, polyethllene glycol, polyvinyl alcohols, polyvinylpyrrolidone, mineral oil, silicone oil, ethylene-vinyl acteate polymers or other low molecular weight polymers soluble in water, lower alcohols or suitable oils.

The compositions of the invention typically contain from about 50 to 99.99%, and preferably about 70 to 99.99%, by weight of the overall enhancer composition mixture comprising the oleic group, the lower $C_2$ or $C_3$ alcohol and inert ingredients within the ranges defined herein. The exact amount of active permeant, and the range of each ingredient used in the enhancer combination may be readily determined by one having ordinary skill in the art. All that is required is that an effective amount of the active permeant be incorporated into the penetration enhancing composition as described, with or without the present of other optional ingredients.

PHARMACEUTICALLY-ACTIVE PERMEANTS

The binary penetration enhancers of the present invention may be formulated to incorporate a broad range of pharmaceutically-active permeants. One of the distinct advantages of these enhancer combinations is that they function to enhance penetration of both lipophilic and hydrophilic permeants including salts and are virtually free from skin irritation effects. The compositions of this invention may be utilized in delivering active permeants to the "target" areas as mentioned in U.S. Pat. No. 4,537,776, i.e. (1) at the surface of the skin; (2) in the stratum corneum itself; (3) in the viable epidermis and upper dermis, just below the stratum corneum; (4) in the various glands and structures in and beneath the dermis (e.g., subcutaneous adipose, dermal vasculature); and/or (5) the general system (i.e. systemic effects).

In view of this, the invention is not limited to any specific type or class of active permeants. Based on the parameters contained herein it is within the ability of one having ordinary skill in the art to determine which permeants can be utilized. Some routine experimentation or testing may be required to determine optimum conditions such as exact concentrations of permeants, ratios of oleic group cell-envelope disordering compounds to alcohols, and the like. Also, some permeants may work best with one particular class of oleic group cell-envelope disordering compounds and/or alcohols. The screening of all possible combinations and ratios of permeants, oleic group cell-envelope disordering compounds and $C_2$ and $C_3$ alcohols has not been attempted.

However, based on the formulation of a representative sampling of diverse active permeants, it is apparent that the binary combination of an oleic group cell-envelope disordering compound and a $C_2$ or $C_3$ alcohol will function to enhance the penetration of a broad spectrum of, pharmaceutically-active permeants. Such agents include, without limitation, those mentioned in U.S. Pat. 4,537,776 such as antimicrobials, antibacterials, antibiotics, antimyobacterials, antimalarials, antiamebics, anthelmintics, antifungals, antivirals, neoplastic agents, agents affecting the immune response, blood calcium regulators, peptide and protein hormones, male sex hormones, female sex hormones, agents useful in glucose regulation, anticoagulants, antithrombotics and hemostatics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, histamine $H_2$-receptor agonists and antagonists, dopamine receptor agonists and antagonists, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, bone-active agents, antiarthritics, vitamins, diagnostic agents and sunscreens. These agents can be used for systemic effect, local activity, or both, as appropriate. Examples of pharmaceutically-active permeants are well-known in the art and can be found listed in sources identified in U.S. Pat. No. 4,537,776 as well as others. For example, active agents, in approved commercially available formulations, their recommended dosages, adverse reactions, side effects and the like are listed in the annual publication of the Physicians' Desk Reference, published by Medical Economics Company, a division of Litton Industries, Inc.

The pharmaceutically-active permeants may be used in the compositions and methods of the present invention at any safe and effective level, or in any safe and effective amount. Dosages will obviously be a function of various variables, such as how active the agent is, how soluble it is in the penetration enhancing composition, how often it is to be applied, whether the use is to be topical (applied to the "afflicted situs") or systemic (applied to the "application situs"), whether two or more active permeants are to be combined, the particular patient being treated, and the like. In any event, the dosage will be the smallest that will achieve the desired result and the period of administration will be as short as possible to attain this result.

In general, dosages and means of application as taught in U.S. Pat. No. 4,537,776 are appropriate to the present invention Levels of active permeants may vary from about 0.01% to about 50% by weight of the total composition with levels of from about 0.01 to 30% being preferred. Levels from about 0.05 to 15% being especially preferred and levels of from about 0.1 to 10% being most especially preferred for some active permeants. However, for some active permeants, it may be required to use more or less than stated above to attain the desired results. Hence, the invention is not directed to any particular amount of active ingredient as long as it is safe and effective.

A compendium of active permeants is contained in U.S. Pat. No. 4,537,776 and published European Patent Application No. 43,738 and incorporated herein by reference. However, for purposes of illustration, a concise listing of active agents follows.

Typical antihypertensive agents which may be utilized include, without limitation, minoxidil, nadolol, pargyline, pindolol, propranolol, reserpine, timolol, trimethaphan, metoprolol, hydrochlorothiazide, hydralazine, furosemide, clonidine, and chlorthalidone.

Diuretics include, without limitation, benzthiazide, buthiazide, cyclopenthiazide, cyclothiazide, metolazone, triamterelene, chlorazanil, clazolimme , and hydroflumethiazide.

Exemplary of anorexigenics are, without limitation, amphetamine, methamphetamine, chlorphentermine, chlortermine, phentermine, phendimetrazine, mazindol, oxazoline, and phenoxyalbyleneamine.

Fungistatic and fungicidal agents encompass, without limitation, thiabendazole, chloroxine, fungimycin, griseofulvin, chlordantoin, salicylic acid, nystatin, clotrimazole, fezatione, sodium pyrithione, amphotericin B, 5-fluorocytosine, haloprogin, vifampin, and pimaricin.

A broad range of analgesics may be utilized including, without limitation, morphine, codeine, heroine, methadone, thebaine, orpiarine, buprenorphine, morphinans, benzomorphans, acetaminophen, butorphanol, diflunisal, fenoprofen, fentanyl, fentanyl citrate, hydrocodone, aspirin, sodium salicylate, ibuprofen, oxymorphone, pentaxicine, naproxen, nalbuphine, mefenamic acid, meperidine and dihydroergotamine.

A typical narcotic antagonist is haloxone. Exemplary antitussive agents include, without limitation, diphenhydramine, guaifenesin, hydromorphone, ephedrine, phenylpropanolamine, theophylline, codeine, noscapine, levopropoxyphene, carbetapentane, chlorpehndianol and benzonatate.

Among the sedatives which may be utilized are, without limitation, chloral hydrate, butabarbital, alprazolam, amobarbital, chlordiazepoxide, diazepam, mephobarbital, secobarbital, diphenhydramine, ethinamate, flurazepam, halazepam, haloperidol, prochlorperazine, oxazepam, and talbutal.

Examples of cardiac drugs are, with limitation, quinidine, propranolol, nifedipine, procaine, dobutamine, digitoxin, phenytoin, sodium nitroprusside, nitroglycerin, verapamil HCl, digoxin, nicardipine HCl, and isosorbide dinitrate.

Antimicrobial agents are inclusive of, without limitation, erythromycin, sulfonamide, lincomycin, clindamycin, tetracycline, chlortetracycline, demeclocycline, doxycycline, and methacycline.

Examples of useful antibacterial agents are, without limitation, phenols, hydroxy benzoic acid, hydroxy quinoline, nitrofuran, nitroimidazoles, oxolinic acid, actinomycetin, bacitracin, tyrothricin, kanamycin, neomycin and chloramphenicol.

A typical antiviral agent is Ara-A. Steroidal anti-inflammatory agents are illustrated by, without limitation, triamcinolone acetonide, beclomethasone dipropionate, hydrocortisone acetate, fluocinolone acetonide, betamethasone valerate, prednisolone, prednisone, methyl prednisolone and paramethasone.

Inclusive of non-steroidal anti-inflammatory agents are acetyl salicylic acid, fenoprofen calcium, ibuprofen, ketoprofen, indomethacin, meclofenamate sodium, mefenamic acid, naproxen sodium, phenylbutazone, and oxyphenbutazone.

Anti-emetics are illustrated by, without limitation, thiethylperazine, metoclopramide, cyclizine, meclizine, prochlorperazine, doxylamine succinate, promethazine, triflupromazine, and hydroxyzine.

A typical dopamine receptor agonist is bromocriptine mesylate. Exemplary amino acid, peptide and protein hormones include, without limitation, thyroxine, growth hormone (GH), interstitial cell stimulating hormone (ICSH), follicle-stimulating hormone (FSH), thyrotropic hormone (TSH), adrenocorticotropic hormone (ACTH), gonadotropin releasing hormone (GnRH) such as leuprolide acetate, vasopressin and their active degradation products Some products may have sufficiently high molecular weights that absorption through the stratum corneum or mucous membranes may be difficult. Therefore, the invention is applicable only to those hormones which have molecular weights and stereo configurations which will allow passage through the skin.

Female sex hormones which can be used include, without limitations, estradiol, diethylstilbestrol, conjugated estrogens, estrone, norethindrone, medroxyprogesterone, progesterone, and norgestrel.

Typical male sex hormones which may be utilized may be represented by, without limitation, testosterone, methyltestosterone, and fluoxymesterone.

The above listed active permeants may, along with others not specifically disclosed, be used separately or in combination according to the treatment regimen desired.

Preferred categories of active permeants include antihypertensive agents, cardiac drugs, analgesics, sedative-hypnotic agents, anti-anxiety agents, steroidal anti-inflammatory agents, non-steroidal anti-inflammatory agents, male sex hormones, and female sex hormones. Those active permeants specifically listed above under each category are particularly preferred.

The components of this invention are inclusive of the active permeants combined with the binary penetration enhancing mixture of oleic group cell-envelope disordering compounds and $C_2$ and $C_3$ alcohols with or without the addition of inert ingredients or diluents. It is contemplated that compositions containing only these ingredients will be sufficient in most instances to obtain the desired results. However, in preparing formulations for actual use, it may be desirable, in addition to inert diluents, to add other components such as excipients, dyes, perfumes fragrances, pacifiers, thickening agents, preservatives, anti-oxidants, gelling agents, surfactants and stabilizers. For example, when forming gels or cremes, it may be desirable to add significant amounts of water, i.e. up to 45% in some cases for gels. Such materials, when added, should not unduly interfere with the penetration enhancement of these compositions. Such formula modifications to improve cosmetic acceptability are well within the skill of workers in the art and do not form part of the present invention.

METHOD OF USE

In any form of medical practice, there are many variables which affect the particular treatment regimen. In that regard, the final diagnosis and treatment is left to the expertise of the practitioner and patient. As previously stated, in clinical practice, it is the goal that the dosage of any active permeant be as small as possible to achieve the result desired and that the administration of the permeant be as short as possible. To attain these conditions, it is imperative that the amount of active ingredient utilized is a safe and effective amount whether applied to an afflicted situs or an application situs. When local treatment is desired, the compositions are applied to the afflicted situs. When systemic treatment is desired, the compositions are applied to an application situs, preferably from a sustained release device such as a patch, bandage, web, film or the like. When both local and systemic treatments are indicated, the compositions can be applied at both the afflicted situs and application situs, or both. The selection of active permeant or combination of permeants, particular penetration enhancement combination and the like are necessarily left to the skill of the practitioner provided the parameters outlined herein are followed.

The dosage, rate of application, place of application, and other treatment parameters are generally outlined in U.S. Pat. 4,537,776 and are incorporated herein by reference rather than being repeated. What is a safe and effective amount of any ingredient will obviously depend upon the active ingredient being used, the site of application, the effectiveness of the penetration enhancer and other parameters outlined herein.

A practitioner being skilled in the art will be able to determine the application parameters of each specific formulation based on the needs of each patient.

EXAMPLES

The following examples demonstrate the penetration enhancement which is obtained by the binary oleic group cell envelope disordering compounds-lower alkanol compositions. In making these tests, human skin consisting of heat-separated abdominal epidermis, taken at autopsy, was placed in a standard Franz diffusion apparatus in a horizontal position between a lower, capped diffusion cell and an upper open cell. A normal saline solution was added to the lower diffusion cell in contact with the subcutaneous side of the skin, and the test composition, consisting of a saturated (unless otherwise indicated) solution of an active drug being monitored formulated in the binary penetration enhancer, was added to the diffusion cell in contact with the upper or epidermal side of the skin.

The cell assembly was kept at a constant temperature of 37° C. At predetermined intervals, the diffusate from the cell on the subcutaneous side of the skin was withdrawn and the amount of drug in the diffusate was measured using standard analytical techniques. Each test was run using a separate skin sample. Unless stated differently, the amount of active drug used was that required to form a saturated solution. The results are reported in terms of flux [mcg/cm2/day (hour)] or relative flux.

EXAMPLE I

To show the penetration enhancement effects of the binary oleic group cell envelope disordering compound-lower alkanol compositions are applicable to active agents inclusive of hydrophilic, salts and hydrophobic agents the following compositions were tested.

| | | Flux [mcg/cm$^2$/day] | | |
|---|---|---|---|---|
| Test No. | Active Ingredient | Propylene Glycol | Glycerol Dioleate (GDO) | GDO/Ethanol (80:20 w/w) |
| I-A | Estradiol | 14.9 | 14.3 | 20.9 |
| I-B | Na-Salicylate | 138.6 | 6,626.0 | 13,696.4 |
| I-C | Ara-A | 0.44 | 0.48 | 3.98 |

The combination of 20% ethanol and 80% GDO shows substantial penetration enhancement effects as compared to a diol (propylene glycol) or GDO alone for all three active agents.

EXAMPLE II

A series of tests similar to Example I were conducted utilizing a greater variety of active agents with various component combinations forming penetration enhancement systems which were directly compared with individual components making up the systems as follows:

| | | FLKUX [mcg/cm2/day] | | | | |
|---|---|---|---|---|---|---|
| Test No. | ENHANCEMENT SYSTEM (% W/W) | Estradiol | Prednisolone | Propranolol HCl | Minoxidil HCl | Sodium Salicylate |
| II-A | 40% OA<br>40% GDO<br>20% EtOH | 75.6 | 915.7 | 1,216.0 | 383.6 | 12,838.0 |
| II-B | 80% OA<br>20% EtOH | 21.2 | 462.0 | 889.0 | 303.0 | 22,905.0 |
| II-C | 80% GDO<br>20% EtOH | 48.6 | 571.0 | 767.0 | 197.0 | 12,541.0 |
| II-D | 95% PG<br>5% OA | 120.1 | 164.0 | 2,259.0 | 1,155.0 | 834.0 |
| II-E | 100% OA | 31.8 | 291.0 | 258.0 | 221.5 | 18,349.0 |
| II-F | 100% EtOH | 18.7 | 81.0 | 45.0 | 23.4 | 1,094.0 |
| II-G | 100% PG | 2.6 | 5.0 | 25.0 | 14.6 | 231.8 |
| II-H | 100% GDO | 12.1 | 92.0 | 257.0 | 62.1 | — |

EtOH = Ethanol
PG = Propylene Glycol
GDO = Glycerol Dioleate
OA = Oleic Acid

The penetration enhancer composition utilized in Test II-D is taught in the prior art and shown in Example XIV of European Patent Application No. 43,738 and generally provides for excellent skin penetration enhancement. However, this combination of oleic acid and propylene glycol causes severe skin irritation. The penetration enhancement systems of Tests II-A, II-B and II-C, with minor exceptions, showed across the board improvement in penetration enhancement over the individual components used alone and generally greater than additive enhancement effects which one would expect when combining these ingredients.

EXAMPLE III

Following the procedure and penetration enhancement systems of Example II, the relative flux of haloperidol as active agent was determined. The results are as follows:

| Test No. | ENHANCEMENT SYSTEM (%w/w) | RELATIVE FLUX Haloperidol |
|---|---|---|
| III-A | 40% OA<br>40% GDO<br>20% EtOH | 19.1 |
| III-B | 80% OA<br>20% EtOH | 10.8 |
| III-C | 80% GDO<br>20% EtOH | 21.7 |
| III-D | 95% PG<br>5% OA | 22.4 |
| III-E | 100% OA | 5.2 |
| III-F | 100% EtOH | 5.1 |
| III-G | 100% PG | 1.0 |
| III-H | 100% GDO | 12.2 |

EtOH = Ethanol
PG = Propylene Glycol
GDO = Glycerol Dioleate
OA = Oleic Acid

It is evident from the above that the combinations of 80% glycerol dioleate and/or oleic acid with 20% ethanol provide penetration enhancement similar to that obtained with propylene glycol and oleic acid and, as will subsequently be demonstrated, does not possess the skin irritation properties of propylene glycol-oleic acid combinations. The enhancement obtained by combining GDO and oleic acid cell-envelope disordering agents with ethanol was far greater than that obtained utilizing the individual components alone.

EXAMPLE IV

Again, following the procedure of the preceding examples, a series of tests utilizing glycerol dioleate and/or oleic acid as cell-envelope disordering components combined with isopropyl alcohol as penetration enhancers, were performed using propranolol HCl and testosterone as active agents. Results are as follows:

| Test No. | ENHANCEMENT SYSTEM (% w/w) | | FLUX [mcg/cm²/day] | ACTIVE AGENT |
|---|---|---|---|---|
| Skin Sample #1 | | | | |
| IV-A | 100% | GDO | 448.8 | Propranolol HCl |
| IV-B | 100% | i-PrOH | 67.2 | Propranolol HCl |
| | 80% | GDO | | |
| IV-C | 20% | i-PrOH | 1,000.8 | Propranolol HCl |
| Skin Sample #2 | | | | |
| IV-D | 100% | GDO | 120.0 | Testosterone |
| IV-E | 100% | OA | 144.0 | Testosterone |
| | 80% | OA | | |
| IV-F | 20% | I-PrOH | 456.0 | Testosterone |
| | 80% | OA | | |
| IV-G | 10% | i-PrOH | 912.0 | Testosterone |
| | 10% | GDO | | |
| Skin Sample #3 | | | | |
| IV-H | 100% | OA | 76.8 | Testosterone |
| | 80% | OA | | |
| IV-I | 20% | i-PrOH | 374.4 | Testosterone |
| | 80% | GDO | | |
| IV-J | 20% | i-PrOH | 384.0 | Testosterone | i-PrOH = Isopropanol
GDO = Glycerol Dioleate
OA = Oleic Acid

The above show that enhancers consisting of oleic group cell-envelope disordering compounds and isopropanol are clearly superior to the individual components used separately.

EXAMPLE V

In copending application Ser. No. 06/930,764, a test was reported showing results of eight different compositions on skin irritation and sensitization. This test, commonly referred to as a "patch insult test" is designed to study both irritation and sensitization. It screens out compositions which are flagrant irritants or sensitizers. However, because the protocol allows a recovery time between applications, it is not a stringent test for irritation since the skin is given a chance to recover between tests. Furthermore, due to the low number of subjects and the relatively short induction phase, this test is not capable of screening out mild sensitizing agents.

A more standard and acceptable model for skin irritation is found in a Primary Skin Irritation (PSI) test utilizing albino rabbits as test subjects. This test, using rabbits, is typically a more sensitive indicator of skin irritation than might be obtained using human subjects.

This test was directed only to a binary enhancer system and no active permeant was involved. The purpose of the test was to get an indication as to at what concentrations ethanol would begin to show significant irritation. The enhancer system, expressed as v/v%, consisted of a constant 10% GMO (glycerol monooleate or monoolein) as the cell envelope disordering compound, and concentrations of ethanol at 25%, 45%, 55% and 75% with the remainder being water. An additional test using 70% ethanol and 30% methyl laurate was also included in the test and is also reported. The compositions tested are listed in Table 1:

TABLE 1

| Formula | Composition |
|---|---|
| 1 | 25/10/65 (Ethanol/GMO/H₂O) |
| 2 | 45/10/45 (Ethanol/GMO/H₂O) |
| 3 | 55/10/35 (Ethanol/GMO/H₂O) |
| 4 | 75/10/15 (Ethanol/GMO/H₂O) |
| 5 | 70/30 (Ethanol/Methyl Laurate) |

Each of these formulations were gelled with 1% w/v Carbopol 1342, (an emulsifying and gelling agent consisting of a copolymer of acrylic acid and long chain alkyl methacrylates). Each sample was evaluated in six (6) albino rabbits. The skin was shaved from the backs of the rabbits 24 hours prior to test sample application. The gelled test samples were applied to the back of the rabbits using 1 cm₂ Finn TM Chambers containing 0.1 cc of test sample. The entire abdomen of the rabbit was then wrapped with surgical tape to prevent the animal from removing the Finn Chambers. After 24 hours of exposure, the Finn Chambers were removed from the backs of the rabbits and any residual test sample adhering to the skin was gently removed with surgical gauze and distilled water. Test sites were scored for erythema and edema one hour and 48 hours following removal according to the scales listed in Table 2.

TABLE II

Evaluation of Skin Reactions

| | Value |
|---|---|
| Erythema and escar formation: | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Edema formation: | |
| No edema | 0 |
| Very slight edema (barely perceptible) | 1 |
| Slight edema (edges of area well defined by definite raising) | 2 |
| Moderate edema (raised approximately 1 millimeter) | 3 |
| Severe edema (raised more than 1 millimeter and extending beyond the area of exposure) | 4 |

Using the above scores, an irritation index (II) was then calculated for each test sample as the sum of all edema and erythema scores in all test animals divided by the number of animals evaluated in each test sample (6) and the number of parameters scored (2; edema+erythema). The scores are reported in Table 3 as follows:

TABLE III

Primary Skin Irritation Index Summary

| Formulation | Irritation Index |
|---|---|
| 1 | .8 |
| 2 | .9 |
| 3 | .8 |
| 4 | 1.7 |
| 5 | 1.7 |

These data indicate that ethanol concentrations of 70 and 75 v/v% produced significant skin irritation whereas ethanol concentrations of 55 v/v% and below produced only about one-half the irritation. Based on these data it is deemed preferable to limit the ethanol concentration in any enhancer system to less than 50%.

EXAMPLE VI

The ability to enhance the penetration of peptide permeants by using enhancers consisting of a mixture of a glycerol oleate ester and ethanol, as compared to a water and ethanol mixture, are shown in this example. A procedure similar to that outlined in Example I was followed except that the flux is reported on an hourly instead of a daily basis The active permeants used were a saturated enhancer solution of bromocriptine mesylate and leuprolide acetate at a loading of 5 mg/ml in the enhancer. The results are as follows:

| Test No. | Active Ingredient | Flux [mcg/cm²/hr] | | |
|---|---|---|---|---|
| | | 60% EtOH 40% GMO | 50% EtOH 50% GDO | 70% EtOH 30% H₂O |
| VI-A | Bromocriptine Mesylate | 1.63 ± 0.08 | — | * |
| VI-B | Leuprolide Acetate | — | 1.33 ± 0.48 | * |

GMO = glycerol monooleate
GDO = glycerol dioleate
* = Below detection limit

These results show that penetration of peptide permeants are clearly enhanced by the use of a combination of either monooleate and dioleate esters of glycerol and ethanol as compared to the use of an aqueous ethanol solution.

EXAMPLE VII

The following are exemplary of other compositions which can be formulated within the scope of this invention. However, they are illustrative only and are not intended to define the scope of the invention. The compositions can be conveniently formulated simply by mixing all components thoroughly. In some formulations, exact percentages are given whereas others are expressed by ranges. All compositions are in present by weight.

| FORMULATION VII-A | | |
|---|---|---|
| Testosterone | | 5–15% |
| Enhancer | | 85–95% |
| Glycerol Dioleate | 5–90% | |
| Ethanol | 5–49% | |
| *PEG 400 | 0–45% | |
| FORMULATION VII-B | | |
| Methadone | | 10–30% |
| Enhancer | | 70–90% |
| Glycerol Dioleate | 20 | |
| Ethanol | 49 | |
| *PEG 400 | 31 | |
| FORMULATION VII-C | | |
| Estradiol | | 0.1–1.0% |
| Enhancer | | 99–99.9% |
| Glycerol Dioleate | 10 | |
| Ethanol | 49 | |
| *PEG 400 | 41 | |
| FORMULATION VII-D | | |
| Ketoprofen | | 10–20% |
| Enhancer | | 80–90% |
| Glycerol Dioleate | 40 | |
| Ethanol | 40 | |
| **PPG 2000 | 20 | |
| FORMULATION VII-E | | |
| Dihydroergotamine | | 1–10% |
| Enhancer | | 90–99% |
| Glycerol Dioleate | 40 | |
| Ethanol | 40 | |
| *PEG 400 | 20 | |
| FORMULATION VII-F | | |
| Nifedapine | | 2–10% |
| Enhancer | | 90–98% |
| Glycerol Dioleate | 45 | |
| Ethanol | 10 | |
| Mineral Oil | 45 | |
| FORMULATION VII-G | | |
| Thiethylperazine | | 1–5% |
| Enhancer | | 95–99% |
| Glycerol Dioleate | 10 | |
| Ethanol | 45 | |
| *PEG 400 | 45 | |
| FORMULATION VII-H | | |
| Metoclopramide | | 10–15% |
| Enhancer | | 85–90% |
| Glycerol Dioleate | 30 | |
| Ethanol | 25 | |
| **PPG 2000 | 45 | |
| FORMULATION VII-I | | |
| Propranolol HCl | | 5% |
| Enhancer | | 95% |
| Glycerol Dioleate | 60 | |
| Ethanol | 20 | |
| *PEG 400 | 20 | |
| FORMULATION VII-J | | |
| Propranolol | | 20% |
| Enhancer | | 80% |
| Glycerol Dioleate | 70 | |
| Ethanol | 20 | |
| **PPG 2000 | 10 | |
| FORMULATION VII-K | | |
| Propranolol HCl | | 5% |
| Enhancer | | 95% |
| Glycerol Monooleate | 6 | |
| Ethanol | 49 | |
| H₂O | 45 | |
| FORMULATION VII-L | | |
| Propranolol | | 15% |
| Enhancer | | 85% |
| Glycerol Trioleate | 20 | |
| Isopropanol | 40 | |
| Mineral Oil | 40 | |
| FORMULATION VII-M | | |
| Fentanyl Citrate | | 2% |
| Enhancer | | 98% |
| Glycerol Monooleate | 6 | |
| Ethanol | 49 | |
| H₂O | 45 | |
| FORMULATION VII-N | | |
| Fentanyl | | 1% |
| Enhancer | | 99% |
| Glycerol Trioleate | 15 | |
| Isopropanol | 45 | |
| Mineral Oil | 40 | |
| FORMULATION VII-O | | |
| Nicardipine | | 5% |
| Enhancer | | 95% |
| Oleyl Alcohol | 10 | |
| Isopropanol | 45 | |
| **PPG 2000 | 45 | |
| FORMULATION VII-P | | |
| Nicardipine HCl | | 10% |
| Enhancer | | 90% |
| Oleic Acid | 2 | |
| Glycerol Dioleate | 10 | |
| Ethanol | 45 | |
| *PEG 400 | 43 | |
| FORMULATION VII-Q | | |
| Naloxone HCl | | 10% |
| Enhancer | | 90% |
| Glycerol Monooleate | 5 | |
| Oleic Acid | 2 | |
| Ethanol | 49 | |
| H₂O | 44 | |
| FORMULATION VII-R | | |
| Naloxone | | 5% |
| Enhancer | | 95% |
| Glycerol Trioleate | 75 | |
| Propanol | 5 | |
| Mineral Oil | 20 | |
| FORMULATION VII-S | | |
| Griseofulvin | | 5% |
| Enhancer | | 95% |
| Glycerol Trioleate | 50 | |
| Isopropanol | 15 | |
| **PPG 2000 | 35 | |
| FORMULATION VII-T | | |
| Fluocinolone Actonide | | 1% |
| Enhancer | | 99% |
| Glycerol Trioleate | 80 | |

FORMULATION VII-U (continued)

| | | |
|---|---|---|
| Isopropanol | 10 | |
| Mineral Oil | 10 | |

FORMULATION VII-U

| | | |
|---|---|---|
| Clindamycin | | 2.5% |
| Enhancer | | 97.5% |
| Oleyl Alcohol | 40 | |
| Isopropanol | 30 | |
| Mineral Oil | 30 | |

FORMULATION VII-V

| | | |
|---|---|---|
| Neomycin Sulfate | | 5% |
| Enhancer | | 95% |
| Glycerol Monooleate | 6 | |
| Ethanol | 49 | |
| H₂O | 45 | |

FORMULATION VII-W

| | | |
|---|---|---|
| Clonidine HCl | | 1% |
| Enhancer | | 99% |
| Glycerol Dioleate | 10 | |
| Ethanol | 45 | |
| *PEG 400 | 45 | |

FORMULATION VII-X

| | | |
|---|---|---|
| Hydroflumethiazide | | 10% |
| Enhancer | | 90% |
| Glycerol Dioleate | 10 | |
| Oleic Acid | 5 | |
| Isopropanol | 45 | |
| *PEG 400 | 40 | |

FORMULATION VII-Y

| | | |
|---|---|---|
| Phentermine | | 5% |
| Enhancer | | 95% |
| Glycerol Trioleate | 60 | |
| Propanol | 10 | |
| Mineral Oil | 30 | |

FORMULATION VII-Z

| | | |
|---|---|---|
| Phentermine HCl | | 10% |
| Enhancer | | 90% |
| Glycerol Monooleate | 6 | |
| Ethanol | 49 | |
| H₂O | 45 | |

FORMULATION VII-AA

| | | |
|---|---|---|
| Mazindol | | 5% |
| Enhancer | | 95% |
| Glycerol Trioleate | 40 | |
| Isopropanol | 20 | |
| **PPG 2000 | 40 | |

FORMULATION VII-BB

| | | |
|---|---|---|
| Morphine Sulfate | | 5% |
| Enhancer | | 95% |
| Glycerol Monooleate | 6 | |
| Oleic Acid | 4 | |
| Ethanol | 45 | |
| *PEG 400 | 45 | |

FORMULATION VII-CC

| | | |
|---|---|---|
| Alprazolam | | 5% |
| Enhancer | | 95% |
| Glycerol Trioleate | 60 | |
| Propanol | 20 | |
| Mineral Oil | 20 | |

FORMULATION VII-DD

| | | |
|---|---|---|
| Ibuprofen | | 10% |
| Enhancer | | 90% |
| Glycerol Trioleate | 20 | |
| Isopropanol | 49 | |
| **PPG 2000 | 31 | |

FORMULATION VII-EE

| | | |
|---|---|---|
| Naproxen Sodium | | 10% |
| Enhancer | | 90% |
| Glycerol Dioleate | 40 | |
| Oleyl Alcohol | 5 | |
| Ethanol | 25 | |
| *PEG 400 | 30 | |

FORMULATION VII-FF

| | | |
|---|---|---|
| Naproxen Sodium | | 10% |
| Enhancer | | 90% |
| Glycerol Monooleate | 6 | |
| Ethanol | 49 | |
| H₂O | 45 | |

FORMULATION VII-GG

| | | |
|---|---|---|
| Progesterone | | 5% |
| Enhancer | | 95% |
| Oleyl Alcohol | 25 | |
| Isopropanol | 30 | |
| *PEG 400 | 45 | |

FORMULATION VII-HH

| | | |
|---|---|---|
| Methyl Testosterone | | 5% |
| Enhancer | | 95% |
| Glycerol Trioleate | 40 | |
| Isopropanol | 40 | |
| **PPG 2000 | 20 | |

*PEG 400 = polyethylene glycol of average molecular weight 400
**PPG 2000 = polypropylene glycol of average molecular weight 2000

While the above examples illustrate numerous embodiments of the invention, the scope is limited only by the operability exhibited by improved enhancement of permeants attributable to the enhancer combination of oleic group components and lower alkanols, with or without added inert diluents. It is to active permeants contained in that enhancer composition that this invention is drawn. It is, therefore, limited in scope only by the appended claims and their functional equivalents.

We claim:

1. A pharmaceutical composition for topical application having penetration-enhancing properties consisting essentially of:
   (a) a safe and effective amount of an active pharmaceutical agent contained in,
   (b) a penetration-enhancing vehicle exclusive of diols and N-cyclic solvents consisting essentially of:
      (i) 1–95% by weight of one or more cell-envelope disordering compounds selected from the group consisting of oleic acid, oleyl alcohol, glycerol esters of oleic acid and mixtures thereof;
      (ii) 5–75% by weight of a lower alkanol selected from the group consisting of ethanol, propanol and isopropanol and mixtures thereof; and
      (iii) 0–45% by weight of an inert diluent.

2. A composition according to claim 1 wherein the lower alkanol is present in amounts of between 5 and 49% by weight.

3. A composition according to claim 2 wherein the active pharmaceutical agent is present in amount ranging from about 0.01 to 50% by weight and the penetration enhancing vehicle is present in amounts ranging from about 50–99.99% by weight.

4. A composition according to claim 3 wherein the cell-envelope disordering compounds are members selected from the following groupings:
   (1) oleic acid and oleyl alcohol or mixtures thereof;
   (2) one or more glycerol esters of oleic acid;
   (3) oleic acid and one or more glycerol esters of oleic acid;
   (4) oleyl alcohol and one or more glycerols ester of oleic acid; and
   (5) mixtures of oleic acid and oleyl alcohol and one or more glycerol esters of oleic acid.

5. A composition according to claim 4 wherein the active pharmaceutical agent is present in amounts ranging from about 0.01 to 30% by weight and the penetration enhancing vehicle is present in amounts ranging from about 70 to 99.99% by weight.

6. A composition according to claim 5 wherein the cell-envelope disordering compound is a member selected from the group consisting of oleic acid and oleyl alcohol and mixtures thereof.

7. A composition according to claim 5 wherein the cell-envelope disordering compound is oleic acid.

8. A composition according to claim 6 wherein the cell-envelope disordering compound is oleyl alcohol.

9. A composition according to claim 5 wherein the cell-envelope disordering compound is a member selected from the group consisting of a one or more glycerol esters of oleic acid.

10. A composition according to claim 9 wherein the cell-envelope disordering compound is glycerol monooleate.

11. A composition according to claim 8 wherein the cell-envelope disordering compound is glycerol dioleate.

12. A composition according to claim 7 wherein the cell-envelope disordering compound is glycerol trioleate.

13. A composition according to claim 5 wherein the cell-envelope disordering compound is oleic acid admixed with a member selected from the group consisting of a one or more glycerol esters of oleic acid.

14. A composition according to claim 13 wherein the cell-envelope disordering compound is glycerol monooleate.

15. A composition according to claim 13 wherein the cell-envelope disordering compound is glycerol dioleate.

16. A composition according to claim 13 wherein the cell-envelope disordering compound is glycerol trioleate.

17. A composition according to claim 5 wherein the cell-envelope disordering compound is oleyl alcohol admixed with a member selected from the group consisting of a one or more glycerol esters of oleic acid.

18. A composition according to claim 17 wherein the cell-envelope disordering compound is glycerol monooleate.

19. A composition according to claim 17 wherein the cell-envelope disordering compound is glycerol dioleate.

20. A composition according to claim 17 wherein the cell-envelope disordering compound is glycerol trioleate.

21. A composition according to claim 5 wherein the alcohol is present in the penetration enhancer vehicle in amounts of between about 20 and 49% by weight.

22. A composition according to claim 4 wherein the inert diluent is present in the penetration enhancer vehicle in amounts ranging from 1 to 45% by weight.

23. A composition according to claim 22 wherein the active pharmaceutical agent is present in amounts ranging from about 0.01 to 30% by weight and the penetration enhancing is present in amounts ranging from about 70 to 99.99% by weight.

24. A composition according to claim 23 wherein the cell-envelope disordering compound is a member selected from the group consisting of oleic acid and oleyl alcohol and mixtures thereof.

25. A composition according to claim 24 wherein the cell-envelope disordering compound is oleic acid.

26. A composition according to claim 24 wherein the cell-envelope disordering compound is oleyl alcohol.

27. A method according to claim 23 wherein the cell-envelope disordering compound is a member selected from the group consisting of a one or more glycerol esters of oleic acid.

28. A composition according to claim 27 wherein the cell-envelope disordering compound is glycerol monooleate.

29. A composition according to claim 27 wherein the cell-envelope disordering compound is glycerol dioleate.

30. A composition according to claim 27 wherein the cell-envelope disordering compound is glycerol trioleate.

31. A composition according to claim 23 wherein the cell-envelope disordering compound is oleic acid admixed with a member selected from the group consisting of a one or more glycerol esters of oleic acid.

32. A composition according to claim 31 wherein the cell-envelope disordering compound is glycerol monooleate.

33. A composition according to claim 31 wherein the cell-envelope disordering compound is glycerol dioleate.

34. A composition according to claim 31 wherein the cell-envelope disordering compound is glycerol trioleate.

35. A composition according to claim 23 wherein the cell-envelope disordering compound is oleyl alcohol admixed with a member selected from the group consisting of a one or more glycerol esters of oleic acid.

36. A composition according to claim 35 wherein the cell-envelope disordering compound is glycerol monooleate.

37. A composition according to claim 35 wherein the cell-envelope disordering compound is glycerol dioleate.

38. A composition according to claim 35 wherein the cell-envelope disordering compound is glycerol trioleate.

39. A composition according to claim 23 wherein the inert diluent is a member selected from the group consisting of water, polypropylene glycol, polyethylene glycol, polyvinyl alcohols, polyvinylpyrrolidone, mineral oil, silicone oil, ethylene-vinyl acteate polymers or other suitable water or oil soluble low molecular weight polymers.

40. A composition according to claim 23 wherein the alcohol is present in the penetration enhancer combination in amounts between about 20 and 49% by weight.

* * * * *

UNITED STATES PATENT AND TRADEMARK OFFICE
CERTIFICATE OF CORRECTION

PATENT NO.  : 4,863,970
DATED       : September 5, 1989
INVENTOR(S) : Dinesh C. Patel, Yunik Chang It is certified that error appears in the above-identified patent and that said Letters Patent is hereby corrected as shown below:

Column 9, line 1, reading "with" should read --without--.

Signed and Sealed this

Eleventh Day of January, 1994

Attest:

BRUCE LEHMAN

*Attesting Officer*          Commissioner of Patents and Trademarks